(12) United States Patent
Laufer et al.

(10) Patent No.: US 9,272,132 B2
(45) Date of Patent: Mar. 1, 2016

(54) MEDICAL DEVICE FOR TREATING AIRWAYS AND RELATED METHODS OF USE

(71) Applicant: Boston Scientific Scimed, Inc., Maple Grove, MN (US)

(72) Inventors: Michael D. Laufer, Menlo Park, CA (US); William Wizeman, Mountain View, CA (US); Noah Webster, Oakland, CA (US); Jerry Jarrard, Longmont, CO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/069,047

(22) Filed: Oct. 31, 2013

(65) Prior Publication Data

US 2014/0128936 A1 May 8, 2014

Related U.S. Application Data (60) Provisional application No. 61/721,789, filed on Nov. 2, 2012, provisional application No. 61/733,295, filed on Dec. 4, 2012.

(51) Int. Cl.
*A61N 1/05* (2006.01)
*A61B 18/12* (2006.01)
(Continued)

(52) U.S. Cl.
CPC .............. *A61N 1/0519* (2013.01); *A61B 18/12* (2013.01); *A61N 1/3601* (2013.01);
(Continued)

(58) Field of Classification Search
CPC ... A61N 1/0519; A61N 1/3601; A61B 18/12; A61B 2018/00488; A61B 2018/00642; A61B 2018/00654; A61B 2018/00875
See application file for complete search history.

(56) References Cited

U.S. PATENT DOCUMENTS 612,724 A 10/1898 Jonathan
1,155,169 A 9/1915 Starkweather
(Continued)

FOREIGN PATENT DOCUMENTS

DE 19529634 A1 2/1997
EP 0189329 A2 7/1986
(Continued)

OTHER PUBLICATIONS

An S.S., et al., "Airway Smooth Muscle Dynamics: A Common Pathway of Airway Obstruction in Asthma," European Respiratory Journal, 2007, 29 (5), 834-860.
(Continued)

*Primary Examiner* — George Evanisko
(74) *Attorney, Agent, or Firm* — Bookoff McAndrews, PLLC (57) ABSTRACT

A medical device for treating an airway of a patient. The medical device may include an elongate tubular member having a proximal end, a distal end, and a lumen extending therebetween. The medical device may also include a plurality of conductive elements disposed on a surface of the elongate tubular member. In some embodiments, at least one of the plurality of conductive elements may be disposed distally of another of the plurality of conductive elements. In addition, each of the plurality of conductive elements may be electrically coupled to a surface of the lumen. The medical device may also include a piston movably disposed within the lumen. The piston may include a distal portion configured to make electrical contact with one or more of the plurality of conductive elements.

19 Claims, 5 Drawing Sheets

(51) Int. Cl.
*A61N 1/36* (2006.01)
*A61B 18/00* (2006.01)

(52) U.S. Cl.
CPC ............... *A61B 2018/00488* (2013.01); *A61B 2018/00642* (2013.01); *A61B 2018/00654* (2013.01); *A61B 2018/00875* (2013.01)

(56) References Cited

U.S. PATENT DOCUMENTS

| | | | |
|---|---|---|---|
| 1,207,479 A | 12/1916 | Bisgaard |
| 1,216,183 A | 2/1917 | Charles |
| 2,072,346 A | 3/1937 | Smith |
| 3,320,957 A | 5/1967 | Edward |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,095,602 A | 6/1978 | Leveen |
| 4,116,589 A | 9/1978 | Rishton |
| 4,129,129 A | 12/1978 | Amrine |
| 4,154,246 A | 5/1979 | LeVeen |
| 4,461,283 A | 7/1984 | Doi |
| 4,502,490 A | 3/1985 | Evans et al. |
| 4,503,855 A | 3/1985 | Maslanka |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,959 A | 8/1988 | Fukasawa |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,907,589 A | 3/1990 | Cosman |
| 4,908,012 A | 3/1990 | Moise et al. |
| 4,944,722 A | 7/1990 | Carriker et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,114,423 A | 5/1992 | Kasprzyk et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,165,420 A | 11/1992 | Strickland |
| 5,167,223 A | 12/1992 | Koros et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |

(56) References Cited

U.S. PATENT DOCUMENTS

| | | |
|---|---|---|
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A * | 2/1997 | Swanson et al. ............ 600/508 |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,641,326 A | 6/1997 | Adams |
| 5,647,870 A | 7/1997 | Kordis et al. |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,735,846 A | 4/1998 | Panescu et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer, Jr. et al. |
| 5,769,846 A | 6/1998 | Edwards et al. |
| 5,772,590 A | 6/1998 | Webster |
| 5,779,669 A | 7/1998 | Haissaguerre et al. |
| 5,779,698 A | 7/1998 | Clayman et al. |
| 5,782,239 A | 7/1998 | Webster |
| 5,782,797 A | 7/1998 | Schweich et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer et al. |
| 5,810,807 A | 9/1998 | Ganz et al. |
| 5,817,028 A | 10/1998 | Anderson |
| 5,817,073 A | 10/1998 | Krespi |
| 5,820,554 A | 10/1998 | Davis et al. |
| 5,823,189 A | 10/1998 | Kordis |
| 5,827,277 A | 10/1998 | Edwards |
| 5,833,651 A | 11/1998 | Donovan et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba |
| 5,924,424 A | 7/1999 | Stevens et al. |
| 5,928,228 A | 7/1999 | Kordis et al. |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,975,303 A | 11/1999 | Morell |
| 5,976,175 A | 11/1999 | Hirano et al. |
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,991,650 A | 11/1999 | Swanson et al. |
| 5,992,419 A | 11/1999 | Sterzer et al. |
| 5,993,462 A | 11/1999 | Pomeranz et al. |

(56) References Cited

U.S. PATENT DOCUMENTS

| | | |
|---|---|---|
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | de la Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,053,909 A | 4/2000 | Shadduck |
| 6,056,744 A | 5/2000 | Edwards |
| 6,056,769 A | 5/2000 | Epstein et al. |
| 6,063,078 A | 5/2000 | Wittkampf |
| 6,071,280 A | 6/2000 | Edwards et al. |
| 6,071,282 A | 6/2000 | Fleischman |
| 6,083,255 A | 7/2000 | Laufer et al. |
| 6,090,104 A | 7/2000 | Webster |
| 6,092,528 A | 7/2000 | Edwards |
| 6,102,886 A | 8/2000 | Lundquist et al. |
| 6,106,524 A | 8/2000 | Eggers et al. |
| 6,123,702 A | 9/2000 | Swanson et al. |
| 6,123,703 A | 9/2000 | Tu et al. |
| 6,139,527 A | 10/2000 | Laufer et al. |
| 6,139,571 A | 10/2000 | Fuller et al. |
| 6,142,993 A | 11/2000 | Whayne et al. |
| 6,143,013 A | 11/2000 | Samson et al. |
| 6,149,647 A | 11/2000 | Tu et al. |
| 6,152,143 A | 11/2000 | Edwards |
| 6,152,899 A | 11/2000 | Farley et al. |
| 6,159,194 A | 12/2000 | Eggers et al. |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,576 B1 | 4/2001 | Tu et al. |
| 6,235,024 B1 | 5/2001 | Tu |
| 6,241,727 B1 | 6/2001 | Tu et al. |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,264,653 B1 | 7/2001 | Falwell |
| 6,269,813 B1 | 8/2001 | Fitzgerald et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,299,633 B1 | 10/2001 | Laufer |
| 6,322,559 B1 | 11/2001 | Daulton et al. |
| 6,322,584 B2 | 11/2001 | Ingle et al. |
| 6,338,727 B1 | 1/2002 | Noda et al. |
| 6,338,836 B1 | 1/2002 | Kuth et al. |
| 6,346,104 B2 | 2/2002 | Daly et al. |
| 6,355,031 B1 | 3/2002 | Edwards et al. |
| 6,379,352 B1 | 4/2002 | Reynolds et al. |
| 6,416,511 B1 | 7/2002 | Lesh et al. |
| 6,416,740 B1 | 7/2002 | Unger |
| 6,423,105 B1 | 7/2002 | Iijima et al. |
| 6,425,895 B1 | 7/2002 | Swanson et al. |
| 6,440,129 B1 | 8/2002 | Simpson |
| 6,442,435 B2 | 8/2002 | King et al. |
| 6,458,121 B1 | 10/2002 | Rosenstock et al. |
| 6,460,545 B2 | 10/2002 | Kordis |
| 6,488,673 B1 | 12/2002 | Laufer et al. |
| 6,488,679 B1 | 12/2002 | Swanson et al. |
| 6,493,589 B1 | 12/2002 | Medhkour et al. |
| 6,494,880 B1 | 12/2002 | Swanson et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,558,378 B2 | 5/2003 | Sherman et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin et al. |
| 6,635,056 B2 | 10/2003 | Kadhiresan et al. |
| 6,638,273 B1 | 10/2003 | Farley et al. |
| 6,640,120 B1 | 10/2003 | Swanson et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |
| 7,131,445 B2 | 11/2006 | Amoah |
| 7,186,251 B2 | 3/2007 | Malecki et al. |
| 7,198,635 B2 * | 4/2007 | Danek et al. ............ 607/96 |
| 7,200,445 B2 | 4/2007 | Dalbec et al. |
| 7,241,295 B2 | 7/2007 | Maguire |
| 7,255,693 B1 | 8/2007 | Johnston et al. |
| 7,266,414 B2 | 9/2007 | Cornelius et al. |
| 7,273,055 B2 | 9/2007 | Danek et al. |
| 7,425,212 B1 * | 9/2008 | Danek et al. ............ 606/47 |
| 7,542,802 B2 | 6/2009 | Biggs et al. |
| 7,556,624 B2 | 7/2009 | Laufer et al. |

(56) References Cited

U.S. PATENT DOCUMENTS

| | | | |
|---|---|---|---|
| 7,740,017 | B2 | 6/2010 | Danek et al. |
| 8,161,978 | B2 | 4/2012 | Danek et al. |
| 8,584,681 | B2 | 11/2013 | Danek et al. |
| 2003/0050631 | A1 | 3/2003 | Mody et al. |
| 2003/0065371 | A1 | 4/2003 | Satake |
| 2003/0069570 | A1 | 4/2003 | Witzel et al. |
| 2003/0187430 | A1 | 10/2003 | Vorisek |
| 2003/0236455 | A1 | 12/2003 | Swanson et al. |
| 2004/0153056 | A1 | 8/2004 | Muller et al. |
| 2004/0249401 | A1 | 12/2004 | Rabiner et al. |
| 2005/0010270 | A1 | 1/2005 | Laufer |
| 2005/0096644 | A1 | 5/2005 | Hall et al. |
| 2005/0171396 | A1 | 8/2005 | Pankratov et al. |
| 2005/0193279 | A1 | 9/2005 | Daners |
| 2005/0240176 | A1 | 10/2005 | Oral et al. |
| 2005/0251128 | A1 | 11/2005 | Amoah |
| 2006/0062808 | A1 | 3/2006 | Laufer et al. |
| 2006/0079887 | A1 | 4/2006 | Buysse et al. |
| 2006/0089637 | A1 | 4/2006 | Werneth et al. |
| 2006/0135953 | A1 | 6/2006 | Kania et al. |
| 2006/0137698 | A1 | 6/2006 | Danek et al. |
| 2006/0247617 | A1 | 11/2006 | Danek et al. |
| 2006/0247618 | A1 | 11/2006 | Kaplan et al. |
| 2006/0247619 | A1 | 11/2006 | Kaplan et al. |
| 2006/0247726 | A1 | 11/2006 | Biggs et al. |
| 2006/0247727 | A1 | 11/2006 | Biggs et al. |
| 2006/0247746 | A1 | 11/2006 | Danek et al. |
| 2006/0282071 | A1 | 12/2006 | Utley et al. |
| 2007/0074719 | A1 | 4/2007 | Danek et al. |
| 2007/0083194 | A1 | 4/2007 | Kunis et al. |
| 2007/0083197 | A1 | 4/2007 | Danek et al. |
| 2007/0100390 | A1 | 5/2007 | Danaek et al. |
| 2007/0106292 | A1 | 5/2007 | Kaplan et al. |
| 2007/0106296 | A1 | 5/2007 | Laufer et al. |
| 2007/0106348 | A1 | 5/2007 | Laufer |
| 2007/0118184 | A1 | 5/2007 | Danek et al. |
| 2007/0118190 | A1 | 5/2007 | Danek et al. |
| 2007/0123958 | A1 | 5/2007 | Laufer |
| 2007/0123961 | A1 | 5/2007 | Danek et al. |
| 2007/0129720 | A1 | 6/2007 | Demarais et al. |
| 2008/0004596 | A1 | 1/2008 | Yun et al. |
| 2008/0255642 | A1 | 10/2008 | Zarins et al. |
| 2009/0030477 | A1 | 1/2009 | Jarrard |
| 2009/0043301 | A1 | 2/2009 | Jarrard et al. |
| 2009/0069797 | A1 | 3/2009 | Danek et al. |
| 2009/0112203 | A1 | 4/2009 | Danek et al. |
| 2009/0143705 | A1 | 6/2009 | Danek et al. |
| 2009/0143776 | A1 | 6/2009 | Danek et al. |
| 2009/0192505 | A1 | 7/2009 | Askew et al. |
| 2009/0192508 | A1 | 7/2009 | Laufer et al. |
| 2009/0306644 | A1 | 12/2009 | Mayse et al. |
| 2013/0218158 | A1 | 8/2013 | Danek et al. |

FOREIGN PATENT DOCUMENTS

| | | |
|---|---|---|
| EP | 189329 A3 | 6/1987 |
| EP | 0282225 A2 | 9/1988 |
| EP | 286145 A2 | 10/1988 |
| EP | 280225 A3 | 3/1989 |
| EP | 286145 A3 | 10/1990 |
| EP | 282225 B1 | 6/1992 |
| EP | 0768091 A1 | 4/1997 |
| EP | 0908150 A1 | 4/1999 |
| EP | 908713 A1 | 4/1999 |
| EP | 908150 B1 | 5/2003 |
| EP | 768091 B1 | 7/2003 |
| EP | 1297795 B1 | 8/2005 |
| FR | 2659240 A1 | 9/1991 |
| GB | 2233293 A | 1/1991 |
| GB | 2233293 B | 2/1994 |
| JP | 59167707 A2 | 9/1984 |
| JP | 7289557 A | 11/1995 |
| JP | 9047518 A2 | 2/1997 |
| JP | 9243837 A2 | 9/1997 |
| JP | 10026709 A2 | 1/1998 |
| RU | 2053814 C1 | 2/1996 |
| RU | 2091054 C1 | 9/1997 |
| SU | 545358 T | 2/1977 |
| WO | WO-8911311 A1 | 11/1989 |
| WO | WO-9502370 A2 | 1/1995 |
| WO | WO-9510322 A1 | 4/1995 |
| WO | WO-9604860 A1 | 2/1996 |
| WO | WO-9610961 A1 | 4/1996 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9858681 A2 | 12/1998 |
| WO | WO-9903413 A1 | 1/1999 |
| WO | WO-9858681 A3 | 3/1999 |
| WO | WO-9913779 A2 | 3/1999 |
| WO | WO-9913779 A3 | 5/1999 |
| WO | WO-9932040 A1 | 7/1999 |
| WO | WO-9934741 A1 | 7/1999 |
| WO | WO-9944506 A1 | 9/1999 |
| WO | WO-9945855 A1 | 9/1999 |
| WO | WO-9964109 A1 | 12/1999 |
| WO | WO-0051510 A1 | 9/2000 |
| WO | WO-0062699 A2 | 10/2000 |
| WO | WO-0062699 A3 | 10/2000 |
| WO | WO-0103642 A1 | 1/2001 |
| WO | WO-0232333 A1 | 4/2002 |
| WO | WO-0232334 A1 | 4/2002 |
| WO | WO-2009082433 A2 | 7/2009 |
| WO | WO-2009137819 A1 | 11/2009 |

OTHER PUBLICATIONS

Bel E.H., ""Hot stuff": Bronchial Thermoplasty for Asthma," American Journal of Respiratory and Critical Care Medicine, 2006, 173 (9), 941-943.
Brown R.H., et al., "Effect of Bronchial Thermoplasty on Airway Distensibility," European Respiratory Journal, 2005, 26 (2), 277-282.
Brown R.H., et al., "In Vivo evaluation of the Effectiveness of Bronchial Thermoplasty with Computed Tomography," Journal of Applied Physiology, 2005, 98 (5), 1603-1606.
Chhajed P.N., et al., "Will there be a Role for Bronchoscopic Radiofrequency Ablation", Journal of Bronchology, 2005, 12 (3), 184-186.
Abandoned U.S. Appl. No. 09/095,323, filed Jun. 10, 1998.
Abandoned U.S. Appl. No. 09/244,173, filed Feb. 4, 1999.
Co-pending U.S. Appl. No. 12/640,644, filed Dec. 17, 2009.
Patented U.S. Appl. No. 12/727,156, filed Mar. 18, 2010.
Patented U.S. Appl. No. 12/765,704, filed Apr. 22, 2010.
Cox G., et al., "Asthma Control during the Year after Bronchial Thermoplasty," New England journal of medicine, 2007, 356 (13), 1327-1337.
Cox G., et al., "Asthma Intervention Research (AIR) Trial Evaluating Bronchial Thermoplasty: Early Results," American Thoracic Society Annual Meeting, 2002, 1 page.
Cox G., et al., "Bronchial Thermoplasty for Asthma," American Journal of Respiratory and Critical Care Medicine, 2006, 173 (9), 965-969.
Cox G., et al., "Bronchial Thermoplasty: Long-Term Follow-Up and Patient Satisfaction," Chest, 2004, 126 (4), 822s.
Cox G., et al., "Bronchial Thermoplasty: One-Year Update, American Thoracic Society Annual Meeting," American Journal of Respiratory and Critical Care Medicine, 2004, 169, A313.
Cox G., et al., "Clinical Experience with Bronchial Thermoplasty for the Treatment of Asthma," Chest, 2003, 124, 106S.
Cox G., et al., "Development of a Novel Bronchoscopic Therapy for Asthma," Journal of Allergy and Clinical Immunology, 2003, 113 (2), S33.
Cox G., et al., "Early Clinical Experience with Bronchial Thermoplasty for the Treatment of Asthma," American Thoracic Society Annual Meeting, 2002, 1068.

(56) References Cited

OTHER PUBLICATIONS

Cox G., et al., "Impact of Bronchial Thermoplasty on Asthma Status: Interim Results from the AIR Trial," 2006, 1 page.

Cox G., et al., "Radiofrequency Ablation of Airway Smooth Muscle for Sustained Treatment of Asthma: Preliminary Investigations," European Respiratory Journal, 2004, 24 (4), 659-663.

Danek C.J., et al., "Bronchial Thermoplasty Reduces Canine Airway Responsiveness to Local Methacholine Challenge," American Thoracic Society Annual Meeting, 2002, 1 page.

Danek C.J., et al., "Reduction in Airway Hyperresponsiveness to Methacholine by the Application of RF Energy in Dogs," Journal of Applied Physiology, 2004, 97 (5), 1946-1953.

Dierkesmann R., "Indication and Results of Endobronchial Laser Therapy," Lung, 1990, 168, 1095-1102.

Global Strategy for Asthma Management and Prevention, National Institute of Health, National Heart, Lung and Blood Institute, 2002, 192 pages.

Hogg J. C., "The Pathology of Asthma," APMIS, 1997, 105 (10), 735-745.

International Search Report for Application No. PCT/US00/05412, mailed on Jun. 20, 2000, 2 pages.

International Search Report for Application No. PCT/US00/18197, mailed on Oct. 3, 2000, 1 page.

International Search Report for Application No. PCT/US00/28745, mailed on Mar. 28, 2001, 6 pages.

International Search Report for Application No. PCT/US01/32321, mailed on Jan. 18, 2002, 2 pages.

International Search Report for Application No. PCT/US98/03759, mailed on Jul. 30, 1998, 1 page.

International Search Report for Application No. PCT/US98/26227, mailed on Mar. 25, 1999, 1 page.

International Search Report for Application No. PCT/US99/00232, mailed on Mar. 4, 1999, 1 page.

International Search Report for Application No. PCT/US99/12986, mailed on Sep. 29, 1999, 1 page.

Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.

James A.L., et al., "The Mechanics of Airway Narrowing in Asthma," American Review of Respiratory Diseases, 1989, 139 (1), 242-246.

Janssen L.J., "Asthma Therapy: How Far have We Come, Why did We Fail and Where should We Go Next ," European Respiratory Journal, 2009, 33 (1), 11-20.

Jeffery P.K, "Remodeling in Asthma and Chronic Obstructive Lung Disease," American Journal of Respiratory and Critical Care Medicine, 2001, 164 (10), S28-S38.

Johnson S. R., et al., "Synthetic Functions of Airway Smooth Muscle in Asthma," Trends Pharmacol. Sci., 1997, 18 (8), 288-292.

Kitamura S., "Color Atlas of Clinical Application of Fiberoptic Bronchoscopy," 1990, Year Book Medical Publishers, 2 pages.

Kraft M., "The Distal Airways: Are they Important in Asthma", European Respiratory Journal, 1999, 14 (6), 1403-1417.

Laviolette M., et al., "Asthma Intervention Research (Air) Trial: Early Safety Assessment of Bronchial Thermoplasty," American Journal of Respiratory and Critical Care Medicine, 2004, 169, A314.

Leff A., et al., "Bronchial Thermoplasty Alters Airway Smooth Muscle and Reduces Responsiveness in Dogs: A Possible Procedure for the Treatment of Asthma," American Thoracic Society Annual Meeting, 2002, 1 page.

Lim E.C., et al., "Botulinum Toxin: A Novel Therapeutic Option for Bronchial Asthma", Medical Hypotheses, 2006, 66 (5), 915-919.

Lombard C.M., et al., "Histologic Effects of Bronchial Thermoplasty of Canine and Human Airways,"American Thoracic Society Annual Meeting, 2002, 1 page.

Macklem P. T., "Mechanical Factors Determining Maximum Bronchoconstriction," European Respiratory Journal, 1989, 6, 516s-519s.

Mayse M.L., et al., "Clinical Pearls for Bronchial Thermoplasty," Journal of Bronchology, 2007, 14 (2), 115-123.

Miller J.D., et al., "A Prospective Feasibility Study of Bronchial Thermoplasty in the Human Airway," Chest, 2005, 127 (6), 1999-2006.

Miller J.D., et al., "Bronchial Thermoplasty is Well Tolerated by Non-Asthmatic Patients Requiring Lobectomy," American Thoracic Society Annual Meeting, 2002, 1 page.

Mitzner W., "Airway Smooth Muscle the Appendix of the Lung," American Journal of Respiratory and Critical Care Medicine, 2004, 169 (7), 787-790.

Mitzner W., "Bronchial Thermoplasty in Asthma," Allergology International, 2006, 55 (3), 225-234.

Netter F.H., "Respiratory System: A Compilation of Paintings Depicting Anatomy and Embryology, Physiology, Pathology, Pathophysiology, and Clinical Features and Treatment of Diseases,In The CIBA Collection of Medical Illustrations M.B. Divertie, ed., Summit: New Jerse," 1979, 7, 119-135.

Notice of final Rejection, Japanese Patent Application No. 2000-553172, dated Sep. 2, 2008, 5 pages.

Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, 62 (12), 18-23.

Rubin A., et al., "Bronchial Thermoplasty Improves Asthma Status of Moderate to Severe Perisstent Asthmatics Over and Above Current Standard-of-Care," American College of Chest Physicians, 2006, 2 pages.

Seow C.Y., et al., "Historical Perspective on Airway Smooth Muscle: The Saga of a Frustrated Cell," Journal of Applied Physiology, 2001, 91 (2), 938-952.

Shesterina M.V., et al., "Effect of Laser Therapy on Immunity in Patients with Bronchial Asthma and Pulmonary Tuberculosis," Problemy Tuberkuleza, 1994, 5, 23-26.

Shore S.A., "Airway Smooth Muscle in Asthma—Not Just More of the Same," New England Journal of Medicine, 2004, 351 (6), 531-532.

Solway J., et al., "Airway Smooth Muscle as a Target for Asthma Therapy," New England Journal of medicine, 2007, 356 (13), 1367-1369.

Sterk P.J., et al., "Heterogeneity of Airway Hyperresponsiveness: Time for Unconventional, But Traditional, Studies," Journal of Applied Physiology, 2004, 96 (6), 2017-2018.

Toma T.P., et al., "Brave New World for Interventional Bronchoscopy," Thorax, 2005, 60 (3), 180-181.

Trow T.K., "Clinical Year in Review I: Diagnostic Imaging, Asthma, Lung Transplantation, and Interventional Pulmonology," Proceedings of the American Thoracic Society, 2006, 3 (7), 553- 556.

UNSW Embryo- Respiratory System [online], Embryology, 2007, [retrieved on Dec. 10, 2007]. Retrieved from the internet: (URL:http://embryology.med.unsw.edu.au/Refer/respire/sclect.htm).

Vasilotta P.L., et al., "I-R Laser: A New Therapy in Rhino-Sino-Nasal Bronchial Syndrome with Asthmatic Component," American Society for Laser Medicine and Surgery Abstracts, 74. 1993.

Vorotnev A.I., et al., "The Treatment of Patients with Chronic Obstructive Bronchitis by Using a Low-power Laser at a General Rehabilitation Center," Terapevticheskii Arkhiv, 1997, 69 (3), 17-19.

Wiggs B.R., et al., "On the Mechanism of Mucosal Folding in Normal and Asthmatic Airways," Journal of Applied Physiology, 1997, 83 (6), 1814-1821.

Wilson S.R., et al., "Global Assessment after Bronchial Thermoplasty: The Patients Perspective," Journal of Outcomes Research, 2006, 10, 37-46.

Wizeman W., et al., "A Computer Model of Thermal Treatment of Airways by Radiofrequency (RF) Energy Delivery," American Thoracic Society Annual Meeting, 2007, 1 page.

Patented U.S. Appl. No. 09/436,455, filed Nov. 8, 1999.

\* cited by examiner

MEDICAL DEVICE FOR TREATING AIRWAYS AND RELATED METHODS OF USE

CROSS-REFERENCE TO RELATED APPLICATIONS

This application claims the benefit of priority from U.S. Provisional Application No. 61/721,789, filed on Nov. 2, 2012, the entirety of which is incorporated by reference herein, and U.S. Provisional Application No. 61/733,295, filed on Dec. 4, 2012, the entirety of which is also incorporated by reference herein.

FIELD

Embodiments of the present disclosure relate generally to medical devices suitable for use in medical procedures for treating conditions causing airway distress, such as, e.g., reversible obstructive pulmonary disease and/or asthma. In particular, embodiments of the disclosure relate to, among other things, medical devices and systems for treating lung airways of varying sizes.

BACKGROUND

Asthma may be a disease in which (i) bronchoconstriction, (ii) excessive mucus production, and/or (iii) inflammation and swelling of airways may occur, causing widespread but variable airflow obstruction, thereby making it difficult for the asthma sufferer to breathe. Asthma may be a chronic disorder, primarily characterized by persistent airway inflammation. Asthma may be further characterized by acute episodes of additional airway narrowing via contraction of hyper-responsive airway smooth muscle (ASM).

Asthma may be a serious condition with a growing number of sufferers and thus needs to be managed appropriately. A number of devices and techniques have been available for treating asthma; those techniques, however, are neither successful nor free from side effects. Overall, conventional devices have not proved sufficiently therapeutic, nor have they been designed to deal with complex asthmatic scenarios. Thus, there exists a need for new methods and/or devices to treat asthma and/or other conditions causing breathing difficulty or distress.

SUMMARY

Embodiments of the present disclosure are directed to medical devices suitable for use in medical procedures for treating conditions causing breathing difficulty or distress, such as, e.g., reversible obstructive pulmonary disease and/or asthma.

In one embodiment, a medical device for treating an airway of a patient may include an elongate tubular member having a proximal end, a distal end, and a lumen extending therebetween. The medical device may also include a plurality of conductive elements disposed on a surface of the elongate tubular member. In some embodiments, at least one of the plurality of conductive elements may be disposed distally of another of the plurality of conductive elements. In addition, each of the plurality of conductive elements may be electrically coupled to a surface of the lumen. The medical device may also include a piston movably disposed within the lumen. The piston may include a distal portion configured to make electrical contact with one or more of the plurality of conductive elements.

Various embodiments of the medical device may include one or more of the following features: some of the plurality of conductive elements may extend radially about the elongate tubular member; the conductive elements may be configured to be activated together or in succession; the conductive elements may be integrally formed with the elongate tubular member; the piston may be configured to electrically couple the plurality of conductive elements to an energy source; at least a portion of the elongate tubular member may be configured to radially deform from a first configuration to a second configuration; a diameter of the elongate tubular member in the second configuration may be larger than a diameter of the elongate tubular member in the first configuration; the piston may include a width larger than the diameter of the elongate tubular member in the first configuration; the piston may include a diameter corresponding to a diameter of the lumen; the piston may be radially expandable; the piston may be configured to transmit energy to at least one of the plurality of conductive elements; and the piston may be configured to transmit energy to all of the plurality of conductive elements. In some embodiments, the piston may be configured to close an electrical circuit so as to allow energy to flow to the plurality of conductive elements.

In another embodiment, a medical device for treating airway tissue may include an elongate tubular member having a proximal end, a distal end, and a lumen extending therebetween. The medical device may also include an expandable basket assembly disposed in the lumen in a collapsed configuration, wherein the basket assembly is configured to expand as it is deployed from the distal end of the elongate tubular member, wherein the basket assembly includes a plurality of legs, wherein each of the plurality of legs includes an electrode, and wherein each of the electrodes is configured to be independently activated.

Various embodiments of the medical device may include one or more of the following features: a sensing element configured to detect basket expansion; and a sensing element configured to monitor impedance.

In one embodiment, a method of delivering energy to an airway tissue may include positioning a medical device within a first portion an airway of a patient, wherein the first portion of the airway includes a first diameter. The medical device may include an expandable basket assembly, wherein the expandable basket assembly includes a plurality of legs, wherein each of the plurality of legs includes an electrode, and wherein each of the electrodes is configured to be independently activated. The method may also include expanding the expandable basket assembly so that the plurality of legs are placed in contact with the airway tissue at the first portion of the airway, determining a first number of electrodes to activate based on a measure of basket expansion, and selectively activating the first number of electrodes to deliver energy to airway tissue.

Various embodiments of the method may include one or more of the following features: the airway tissue may include airway smooth muscle; each of the plurality of legs may include a plurality of electrodes; repositioning the medical device within a second portion of the airway, wherein the second portion may include a second diameter larger than the first diameter; expanding the expandable basket assembly so that the plurality of legs are placed in contact with the airway tissue at the second portion of the airway; determining a second number of electrodes to activate based on a measure of basket expansion and/or impedance; selectively activating the second number of electrodes to deliver energy to airway tissue; and the medical device may include an elongate member having a lumen configured to receive the expandable basket assembly.

It may be understood that both the foregoing general description and the following detailed description are exemplary and explanatory only and are not restrictive of the invention, as claimed.

DETAILED DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device into a patient. By contrast, "proximal" refers to the end closest to the medical professional when placing a device in the patient as intended.

Overview

Embodiments of the disclosure describe medical devices for treating lung conditions causing breathing distress. More particularly, the disclosure relates to devices and methods for treating airways of varying sizes by delivering energy to airway tissues, such as, e.g., ASM tissue. More specifically, energy may be delivered to a length of airway tissue in successive sections by a tubular member equipped with sets of longitudinally spaced conductive elements or electrodes. The tubular member may be inserted into a target airway and one or more of the conductive elements may be energized together or in succession, thereby applying energy to portions of airway tissue. The energy may ablate and/or reduce the amount of targeted tissue (e.g., ASM) in the airway. As a result, airway tissues, such as, e.g., ASM, are reduced and/or have reduced ability to constrict and/or to impede the flow of air through the airway. This treatment can ameliorate the effects of asthma and other breathing conditions.

Exemplary Embodiment

Figure 1A:
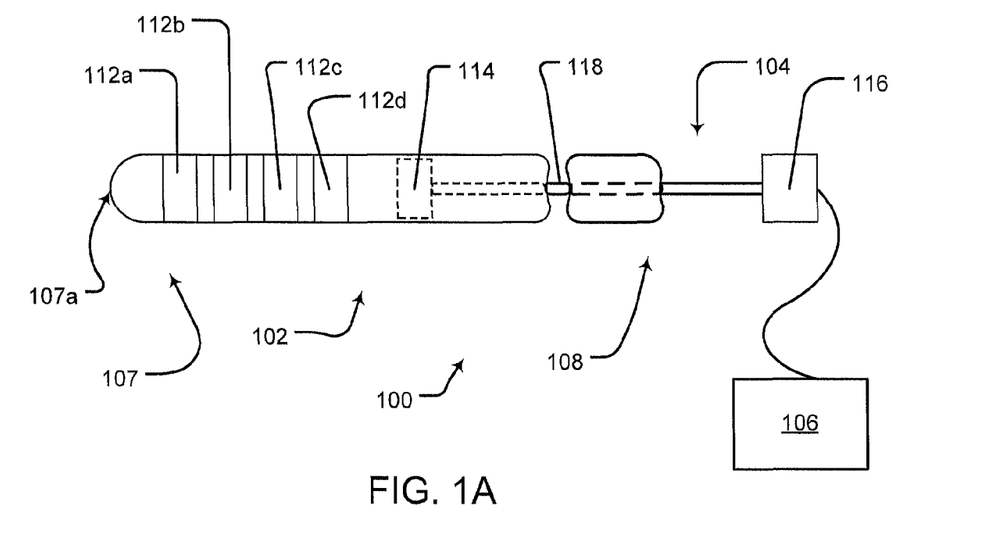
FIG. 1A is a side view of a medical device, according to an embodiment of present disclosure.

FIG. 1A depicts a side view of a medical device 100 for treating breathing conditions, including, e.g., asthma and reversible obstructive pulmonary disease. The medical device may include a tubular member 102 and a piston assembly 104. Tubular member 102 may be a generally elongate and hollow member, which may include a proximal end 108 and a distal end 107, with a generally circular cross-section. Alternatively, cross-sectional shapes including semi-circular, rectangular, cylindrical, oval, or other suitable shapes may also be contemplated as appropriate for use in the intended environment. The tubular member 102 may define an interior lumen 109. In some embodiments, the tubular member 102 may define a plurality of lumens (not shown), with some of the plurality of lumens extending the entire length of the tubular member 102, and the remaining lumens only extending partly through tubular member 102, as discussed below in greater detail. In some embodiments, the tubular member 102 may include a catheter. The catheter may include flexibility sufficient to allow it to traverse tortuous airway passages. In some embodiments, the catheter may be a generally long, flexible tube that may be inserted into the body for diagnosis or treatment, for example. Typically, the catheter may include a proximal end and a distal end; the distal end may be made of a softer material or be more flexible than the proximal end so that the catheter may more easily navigate, e.g., a patient's airway passages. The flexible portion may be formed from any suitable flexible materials such as low-density polyethylene, among others. In other embodiments, the catheter may be flexible along its entire length or adapted for flexure along portions of its length. Furthermore, the catheter may include any suitable steering mechanism for selectively positioning a distal portion of the catheter. Such steering mechanisms may include, but are not limited to, pull wires, pulley mechanisms, and gears, and/or motorized actuators. Interior lumen 109, shown in FIG. 1B, may extend the length of tubular member 102. In some embodiments, however, lumen 109 may extend only partially along the length of tubular member 102. Proximal end 108 may have an opening, as explained in more detail below, and distal end 107 may be open or closed, depending on design considerations. For example, a closed, curved distal end portion 107a may facilitate maneuvering tubular member 102 into a desired operational site in the patient's airway. Distal end portion 107a may include an atraumatic configuration, so that damage to surrounding tissues is minimized when tubular member 102 is advanced into a patient's airways. Alternatively, an open-ended distal end portion 107a may promote airflow through the tubular member 102, as well as facilitate reciprocal movement of portions of the piston assembly 104, as discussed in more detail below. The opening (not shown) in distal end portion 107a may be in communication with lumen 109, allowing tubular member 102 to deliver irrigation or additional medical devices into the patient. For example, a distal portion of lumen 109 may include an illumination source configured to provide light through an opening in distal end portion 107a. In addition, lumen 109 may include one or more optical or imaging devices configured to allow a user to visualize body portions distal of tubular member 102.

In some embodiments, tubular member 102 may be removably mounted on the distal end of a catheter or, as alluded to above, tubular member 102 may be a catheter modified as set out herein. In one embodiment, the catheter may be introduced through a bronchoscope, endoscope, or other suitable introduction device into a bodily conduit or airway.

As alluded to above, tubular member 102 may be a flexible or rigid member adapted to be inserted into a patient. Further, the tubular member 102 may be flexible in certain portions and rigid in others. For example, the tubular member's distal end 107 may be flexible or steerable, allowing the member to traverse circuitous cavities or lumens, while the rest of the member may be rigid to allow the tubular member 102 to be inserted into a body cavity. Further, tubular member 102 may have a uniform diameter or may be tapered at the distal end 107 to facilitate insertion into a patient's body. Depending upon the particular implementation and intended use, the length and configuration of the tubular member 102 may vary.

With continuing reference to FIG. 1A, an outer surface of tubular member 102 may include a number of energy delivery elements. In some embodiments, the energy delivery elements may include electrically conductive elements 112a, 112b, 112c, 112d (collectively 112). Elements 112a-112d may include electrodes. Energy passes from these conductive elements 112 to the desired treatment region. The conductive elements 112 can have varying sizes, shapes, physical properties, numbers, thickness, spacing, distribution and/or densities. The conductive elements 112 can be metallic arrays, electrode segments, or other electrically conductive mediums that can conduct sufficient energy to targeted tissue portions. For a person skilled in art, it is understood that the actual number and shape of electrodes may vary according to the intended application. The conductive elements 112 may be configured to operate at a frequency desired for an intended environment. Each element 112a-112d may be formed of a biocompatible, electrically conductive material, including, but not limited to, polymers, metals (e.g., such as stainless steel, copper, silver, nickel, and gold), blends, alloys (e.g., nitinol), combinations thereof, applied as a thin band or strip of material disposed at least partially on tubular member 102. In some embodiments, however, one or more of elements 112a-112d may completely encircle tubular member 102. Each element 112a-112d may be adhered to tubular member 102 by suitable techniques known in the art, such as adhesive bonding, welding, or the like. In addition, one or more of elements 112a-112d may be integrally formed with the remainder of tubular member 102 by any suitable means known in the art. For example, elements 112a-112d may be molded into tubular member 102. In some embodiments, the conductive elements 112 may be printed onto tubular member. In such embodiments, conductive elements 112 may be configured to change in size and/or shape as the tubular member may expand or contract. More particularly, in the embodiment where conductive elements 112 may be printed on a surface of tubular member 102, conductive elements 112 may be configured to expand as tubular member 102 expands. Thus, each conductive element 112 may expand and/or the spacing between each adjacent conductive element 112 may increase.

It should be noted that elements 112a-112d may be preferably formed of a thickness that does not impede the ability of the member 102 to navigate a patient's airway. For example, one or more of elements 112a-112d may be substantially flush with a remainder of tubular member 102. Alternatively, one or more elements 112a-112d may be slightly offset relative to an outer surface of tubular member 102. Furthermore, the number of conductive elements provided on tubular member 102 may be varied to fit a therapeutic scenario, for example. Although four conductive elements are shown in FIG. 1A, a larger or smaller number of elements may be provided, as dictated by the needs of a particular planned treatment regimen. Still further, those of ordinary skill in the art will understand that elements 112a-112d may be disposed on tubular member 102 in any suitable configurations, including, but not limited to, parallel to one another, offset from one another, or at selected angles to one another.

Figure 1B:
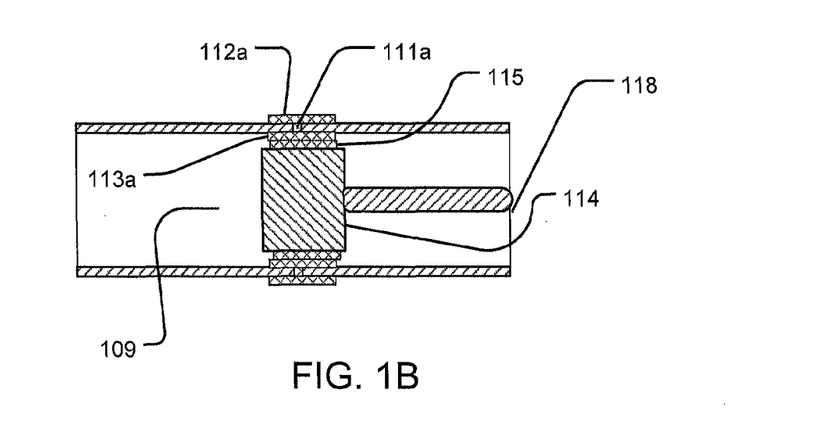
FIG. 1B is a longitudinal sectional view of a portion of the medical device of FIG. 1.

FIG. 1B is a longitudinal sectional view of a portion of the tubular member 102. As seen in FIG. 1B, element 112a, which is depicted as being disposed on or adjacent an outer surface of tubular member 102, may have a corresponding inner element 113a, for example, disposed on or adjacent an inner surface of tubular member 102. The structure and method of applying inner element 113a may be substantially similar to the corresponding structure and attachment methods discussed above for elements 112a-112d. Corresponding element pairs, such as, e.g., element 112a and inner element 113a, may be operably coupled by one or more connecting members 111a. The connecting members 111a may provide both electrical and mechanical connection between elements 112a and 113a. In one embodiment, the connecting member 111a may be a rivet. In other embodiments, connecting member 111a may be mechanical joint created of, for example, solder. Each connecting member 111a may be attached to respective surfaces of outer element 112a and inner element 113a, projecting through an appropriately sized aperture formed in a wall of tubular member 102. The coupling also can be accomplished by adhesive bonding, welding, brazing, or the like. The number of rivet members 111a attached to a given pair of elements 112, 113 may be selected by those of skill in the art, taking into consideration factors of assembly methods and contributions to the rigidity of the overall device. That is, any suitable number of rivet member 111a may be provided for a pair of elements 112a and 113a, providing suitable electrical coupling between the two. Each rivet member 111a may be electrically conductive, providing complete electrical connectivity between outer conductive element 112a and inner element 113a. In some embodiments, rivet member 111a and elements 112a and 113a may be fabricated from a one-piece construction.

Returning to FIG. 1A, piston assembly 104 may include a piston element 114, a handle 116, and an actuation element 118 extending between them. The piston element 114 may transmit the energy in monopolar or bipolar modes. In the monopolar mode, energy transmitted by the piston element 114 is such that each conductive element 112 has the same polarity—either as cathode or as anode, but in the bipolar mode, each conductive element 112 may have opposite polarity—cathode and anode. It should be noted that the embodiments disclosed herein may be operable with both direct current (DC) and alternating current (AC), such as, e.g., RF. Further, as those of ordinary skill in the art will recognize, in monopolar embodiments, the device may include a "ground" electrode or conductive element while one or more active electrode or conductive elements may be disposed on tubular member 102. In bipolar embodiments, on the other hand, a plurality of electrodes or conductive elements may be disposed on the tubular member 102 and disposed proximate tissue targeted for treatment. Thus, the use of "cathode" or "anode" should not be construed as limiting to either DC or AC. It should be noted that the proximal end 108 may remain outside the patient's body. In embodiments where medical device 100 may be used in conjunction with a separate catheter or introduction sheath (not shown), for example, the entire tubular member 102 may be configured to be advanced into a patient's body through the separate catheter or introduction sheath, with the proximal end of the separate catheter or introduction sheath remaining outside. It should also be noted that proximal end 108 of either the tubular member 102 or the separate catheter or introduction sheath may further include a handle, a mounting device, or other components known in the art for use in conjunction with minimally invasive techniques. No matter which of these techniques may be employed, at least the handle 116 may remain outside the patient's body.

Piston element 114, as best seen in FIG. 1B, may fit slidably inside lumen 109, moving reciprocally inside the lumen 109 to make selective electrical contact with one or more sets of inner elements 113a-113d. Thus, piston element 114 may be configured (e.g., sized and shaped) to fit into lumen 109. In the illustrated embodiment, piston element 114 may be a solid element, but it could be formed as a hollow cylinder, with one or both open ends, as desired. Contact element 115 may be carried on the outer surface of piston element 114, sized to make electrical contact with one or more inner elements 113a-113d. Contact element 115 may be electrically coupled to piston element 114 by any suitable conventional technique, as noted above. In addition, contact element 115 may be fabricated of a one-piece construction with piston element 114. In one embodiment, piston element 114 may contact inner element 113a, e.g., at one location, i.e., the point where contact element 115 touches inner element 113a. In other embodiments, piston element 114 may make contact with inner element 113a in a plurality of locations. In embodiments that do not include an inner element 113, e.g., contact element 115 may contact conductive element 112 directly. Further, although the depicted embodiments illustrate a single contact element 115, piston element 114 may include a greater or lesser number of contact elements.

In one embodiment, it may be possible transfer energy from piston element 114 to conductive elements 112 via induction. That is, it may not be necessary to include contact element 115 and/or contact element 113a, nor would it be necessary to have contact element 115 physically touch contact element 113a. For example, in one instance, piston element 114 may include a coil. Similarly, conductive elements 112 may include a coil or be operably coupled to a coil. In the described embodiment, therefore, energy may be transferred by induction from the coil of piston element 114 to the coils associated with conductive elements 112. The transfer may occur without any physical contact, direct or indirect, between conductive elements 112 and piston 114.

Piston assembly 104 may further include an actuation element 118, extending proximally from piston element 114 to the handle 116. Actuation element 118 may be configured to reciprocally move the piston element 114 (in response to movements imparted on or by handle 116) within lumen 109 and conduct energy (e.g., electrical or RF energy) from an energy generator to piston element 114. To perform the actuation function, actuation element 118 may be formed of wire, rod, or a wire-like structure having sufficient stiffness to move the piston element 114 reciprocally within lumen 109. In other embodiments, the actuation element 118 may include more than one wire or rod, and these may include a braided structure. In addition, the dimensions and configuration of actuation element 118 may vary from embodiment to embodiment. For example, the actuation element 118 may include a substantially circular cross-sectional configuration. In some embodiments, the device 100 may include a suitable locking element for maintaining a position of the actuation element 118 and/or the piston element 114 relative to tubular member 102. Various examples of the locking element may include wire springs, flaps or others as known in the art. To provide energy to piston element 114, actuation element 118 may be formed of a suitable conductive material, such as, e.g., copper wire, which may be suitably insulated or otherwise isolated from surrounding components.

In a further embodiment, piston element 114 may be reciprocally moved within lumen 109 via, e.g., a hydraulic or pneumatic force. For example, a fluid (such as, e.g., an incompressible fluid) may be provided to advance piston element 114 forward. Similarly, a fluid may be withdrawn to retract piston element. In some embodiments, a vacuum or otherwise negative pressure may be used to facilitate withdrawal of the fluid.

As alluded to above, piston assembly 104, may be electrically coupled to a suitable energy source 106. Although one embodiment describes energy in the form of electrical current, energy provided by device 100 may include any suitable alternative energy type, including, but not limited to RF, ultrasound, and/or cryogenic. Depending on the type of energy provided by device 100, energy source 106 and actuation element 118 may be accordingly configured to generate and transmit such energy in an efficient manner that minimizes energy losses to the environment. For example, in embodiments where electrical energy is delivered, energy source 106 may be an electrosurgical generator, and actuation element may include conductive elements in the form of wires.

The piston element 114 may be formed of any suitable biocompatible material, such as polyurethane, plastics, polymers, and metals. The piston element 114 may also be coated with antibacterial and/or lubricious agents that prevent bacterial infections. Similarly, the tubular member 102 may be coated with lubricious materials and/or antibacterial agents to ease insertion into tight lumens or cavities, and to prevent infections, respectively. Further, portions of the tubular member 102 may include radiopaque materials or markings to assist in visualizing the position of tubular member 102 within a patient's body. Tubular member 102 described here may be any well-known endoscopic device used for colonoscopy, resectoscopy, cholangioscopy, or mucosal resection, and thus, this device will not be discussed in detail in the remainder of the disclosure.

In some embodiments, piston element 114 can be moved automatically or manually either with the rate determined empirically or with feedback from a suitably positioned sensor, such as, e.g., a temperature sensor, or visual feedback. To this end, the medical device 100 may include a thermal sensor (not shown), such as, e.g., a thermocouple, resistance temperature detectors, full system thermometers or others, adapted for monitoring the temperature of the conductive elements 112a-112d, the airway wall, or any desired portion of device 100. The thermal sensor may be placed on or adjacent the tubular member 102 or the piston element 114. In additional embodiments, the medical device 100 may include sensors for measuring the size of patient's airway or position of the tubular member 102 within the patient's body.

In certain implementations, the device 100 may include a suitable controller adapted for monitoring various control therapies. The control therapies may include suitable algorithms or treatment plans. These control therapies may facilitate delivering appropriate energy to airway tissues upon activation of one or more conductive elements 112. One control therapy may include activating one conductive element at a time, e.g., element 112a, for example, deactivating that element, and subsequently activating another conductive element 112b. The conductive elements 112 may have an activation duration of approximately 5-15 seconds. In another exemplary control therapy, multiple conductive elements 112a-112d may be simultaneously activated for either the same or differing durations. Further, in some embodiments, one or more of elements 112a-112d may be configured to deliver energy in quantities different from the quantities of energy delivered by the other of elements 112a-112d.

As the piston element 114 slides within lumen 109, contact element 115 makes contact with successive inner elements 113a-113d, energizing each element in turn. As noted above, energy can be delivered in a number of forms, such as, e.g., RF energy in either a monopolar or a bipolar manner, as well as other forms of energy, such as conducted heat energy from resistively heated elements, cryogenic energy, and/or electrical energy. The number and arrangement of the conductive elements 112a-112d may vary depending on the pattern of energy delivery desired. In some embodiments, tubular member 102 can be used to deliver radiant or heat energy to the airway. Other embodiments may deliver indirect radio frequency, microwave energy, or conductive heat energy to the tissue. In cases of heat energy generated by resistive heating, for example, the electrical current provided to the resistive devices may be AC or DC, and AC may be delivered in the RF range. The use of RF energy provides an added safety feature of minimizing the possibility of harm to the patient caused by escaped current. The device may also use a combination of different types of energy.

As the piston element 114 is moved, sequential conductive elements 113 are brought in contact with the contact element 115 and are activated to treat the airway. In some embodiments, the piston element 114 may displace (e.g., by pushing) the energized conductive element 113 energized into contact with the bodily conduit. In addition, the piston element 14 may be elastic, expandable, inflatable, to optimize contact between the tubular member 102 and body tissues.

According to the embodiment of FIG. 1, only one conductive element 112 may be activated at a time. In addition, or alternatively, multiple conductive elements 112 may be energized together or in succession to apply energy to multiple portions of airway tissues. It will be understood that alternative piston mechanisms could energize various other combinations of conductive elements 112 to produce other energy delivery regimes, as might be desired for particular circumstances. For example, rather than expanding a size of tubular member 102, each of the conductive elements 112 may be multiplexed together. As discussed above, the conductive elements 112 may be energized all together or one by one. The energy may ablate and reduce, e.g., by debulking, the amount of targeted tissue in the airway.

The inner elements 113a-113d can be formed using any suitable biocompatible material. Examples of suitable materials include metals, alloys, conductive polymers, and conductive carbon. The number of elements 113 may vary depending on the number of the conductive elements 112. For example, there may be two, four, six, eight, ten, twelve, fourteen, sixteen, or more sets of conductive elements 112, and a corresponding number of inner elements 113. As will be recognized, other suitable numbers of conductive elements may also be contemplated. The inner elements 113 may be soldered or adhered to the tubular member 102 using adhesives. In one embodiment, one or more of the conductive elements 112 and elements 113 may be formed integrally. One technique may include forming the conductive elements 112 and elements 113 integrally by molding both of them with tubular member 102.

In certain implementations, elements 113 may not be present, so in such cases, the conductive elements 112 may be embedded in a sidewall of tubular member 102, with an outer surface configured to be in contact with tissue and an inner surface configured to contact, directly or indirectly, piston element 114. The surfaces of the conductive elements 112 may be flush with or protrude relative to the respective surface of the tubular member 102.

The tubular member 102 may be delivered inside the body with or without visualization. In one example, an embodiment may utilize marker dyes or cameras to visualize the exact location of the target tissue. In other embodiments, radiopaque material could be applied to selected locations on tubular member 102, allowing an operator to identify its location with an appropriate visualization device. It will be understood, however, that these embodiments are not exhaustive and that many other configurations are conceivable and within the scope of the present disclosure.

Figure 2:
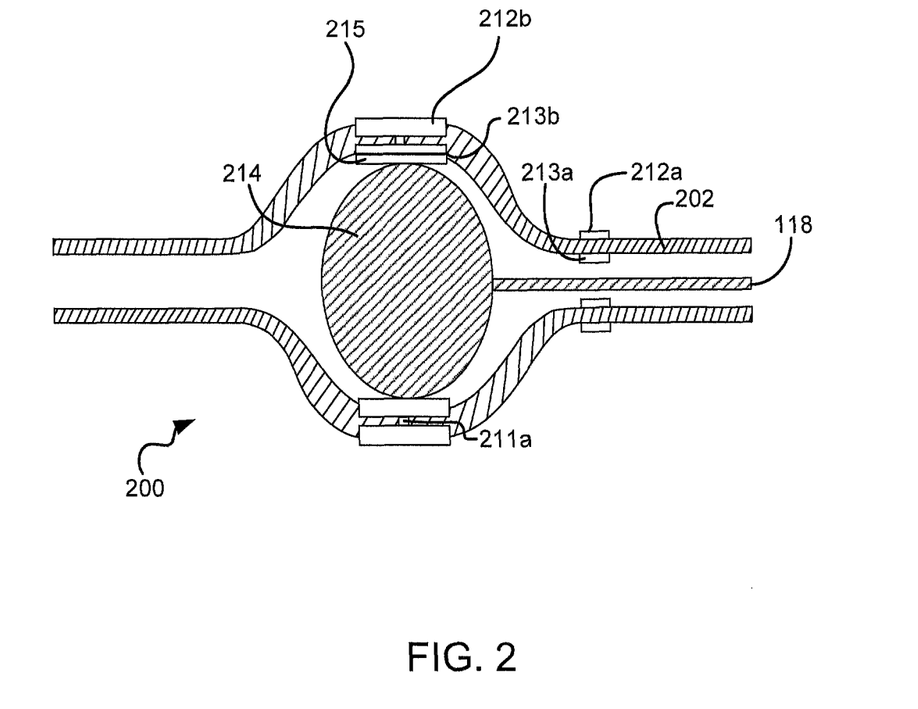
FIG. 2 is a longitudinal sectional view of a portion of a medical device, according to an alternative embodiment of the present disclosure.

FIG. 2 is a cross-sectional view of an alternative embodiment of a medical device 200, designed to overcome the requirement that tubular member 102 have a cross sectional dimension sufficiently large enough to make contact with the patient's airway wall. The embodiment depicted in FIG. 2 may include one or more features of the other embodiments disclosed herein. For example, the portion of medical device 200 shown in FIG. 2 corresponds to the portion of medical device 100 shown in FIG. 1A. Medical device 200 may include a tubular member 202 and a piston element 214. Apart from these two elements, it should be understood that medical device 200 may be substantially similar to medical device 100. Thus, elements such as the handle 116, energy source 106, and associated elements will not be discussed further in regard to this embodiment. Furthermore, tubular member 202 may include sets of conductive elements 212 and inner elements 213 generally similar to those discussed in connection with FIG. 1.

Tubular member 202 may be formed from suitable elastic materials capable of temporary deformation/expansion, including, but not limited to, ePTFE and PTFE.

In one embodiment, the device 200 may include anchoring members for fixing/securing the tubular member 202 in a position during treatment session, for example. For example, tubular member 202 may have one or more expandable baskets/balloons that can be expanded to center or secure tubular member 202 in an airway lumen.

Tubular member 202 may be sized to be smaller in diameter than the airway targeted for treatment, which allows for relatively easy insertion and navigation of tubular member 202 to the treatment location. Piston element 214, however, may be an element dimensioned so that its cross-sectional diameter, together with the wall thickness of tubular member 202, may generally correspond to the expected diameter of the airway to be treated. In other words, piston element 214 may have a diameter larger than that of tubular member 202, such that the wall material of tubular member 202 may be pushed outward by piston element 214 as piston element 214 is advanced through tubular member 202. In other words, portions of tubular member 202 may expend as piston element 214 passes into and/or through those portions. In this manner, an outer surface of a wall of tubular member 202 may be brought into contact with airway tissue by, for example, deflection of the wall. In some embodiments, peripheral portions of tubular member 202 may be configured to expand uniformly and/or symmetrically. That is, each portion of tubular member 202 about a central longitudinal axis of tubular member 202 may expand the same amount as other portions of tubular member 202. In other embodiments, however, it may be desirable to treat non-circular airways. In such embodiments, various portions of tubular member 202 may be configured to expand by differing amounts. For example, expansion of tubular member 202 may be asymmetrical about a central longitudinal axis. Thus, in such embodiments, tubular member 202 when expanded may be capable of uniformly making contact with an airway wall of a non-circular airway. Further, as those of ordinary skill will recognize, asymmetrical expansion to accommodate airways having varying geometries may unpredictably change a spacing between adjacent conductive elements 112. In such cases, therefore, it may be desirable to adjust an amount of delivered energy. Thus, the principles of the present disclosure contemplate measuring a distance between adjacent electrodes after tubular member 202 is expanded irregularly. The measurement may be used to empirically determine and adjust a level of energy to be delivered. Alternatively, energy may be first delivered in small quantities and a tissue reaction or characteristic may be measured. Based on this measurement, the delivered energy levels may be adjusted.

In the same manner as discussed above, tubular member 202 may include a number of conductive elements 212a-212b (collectively 212) and inner elements 213a-213b (collectively 213). In some embodiments, the conductive elements may be electrodes. In addition, as described above in connection with FIG. 1, a rivet member 211a may provide electrical connection between conductive element 212 and inner element 213. Contact member 215 may be disposed on piston element 214 and positioned and sized to make contact with one or more of inner elements 213. Furthermore, contact member 25 may be electrically coupled to actuating element by any suitable connection known in the art. Conductive elements 212 and inner elements 213 may differ from their counterparts in that they may be formed from an elastic or otherwise deformable material, which may allow elements 212 and 213 to be deformed along with the material of tubular member 202. In one embodiment, for example, element 212 may be formed of a conductive coating applied to the outer surface of a deformable wall of tubular member 202. In other embodiments, an outer wall of the tubular member 102 may be deformable, while other portions are not deformable. Still further, some portions of tubular member 102 may be deformable to a greater degree than other portions of tubular member 102.

In the embodiment of FIG. 2, therefore, tubular member 202 may be positioned within an airway, and piston element 214 may be advanced in sequential increments, with each sequential increment bringing one or more of conductive elements 212 into contact with airway tissue. With the piston element 214 in position, energy can be applied through the piston element 214 to the elements 212, 213, respectively, as discussed above. More particularly, as the piston element 214 is moved within the lumen 109, it may activate conductive element 112a, for example, and further, when the piston 214 is moved distally within the lumen 109, the conductive element 112a is out of electrical communication and thus, it is deactivated. Subsequently, conductive element 112b is activated. This process repeats so that successive conductive elements are activated. In some embodiments, for example, a conductive element 112 may not be deactivated before the next conductive element is activated. Thus, a plurality of conductive elements 112 may be activated simultaneously.

In some embodiments, piston element 214 may be expandable. For example, piston element 214 could be constructed as an expandable balloon, cage or basket, which may be longitudinally movable inside a lumen of tubular member 202. Here, the expandable structure may be inflated using conductive fluid or other suitable mechanisms known in the art. In such embodiments, piston element 214 can be moved into position so that its expansion may deform an outer wall of tubular member 202 to bring, for example, a conductive element 212 into contact with airway tissue. Treatment then may proceed as discussed above, followed by a contraction of piston element 214 and movement of that element to a next treatment position. Accurate positioning of piston element 214 can be accomplished by radiopaque markers and the aid of suitable imaging techniques. Further, in some embodiments, the energy delivered to tissue may be monitored and used to track a position of the catheter and chart treatments without the need for radiation-based imaging. For example, the delivered energy may be visualized by, e.g., infrared and/or thermal imaging. In addition, the delivered energy may be used to empirically determine one or more characteristics of treatment. Moreover, expansion and contraction of piston element 214 can be implemented using conventional techniques widely employed on expandable balloon devices. Those of skill in the art are well capable of adapting existing devices to the embodiments discussed here. In some embodiments, the entire tubular member 202 may be energized by proximal electrodes coupled directly to an energy source. Herein the entire length of the tubular member 202 can be electrically active, and the piston brings the active segment into contact with the tissue targeted for treatment.

Figure 3:
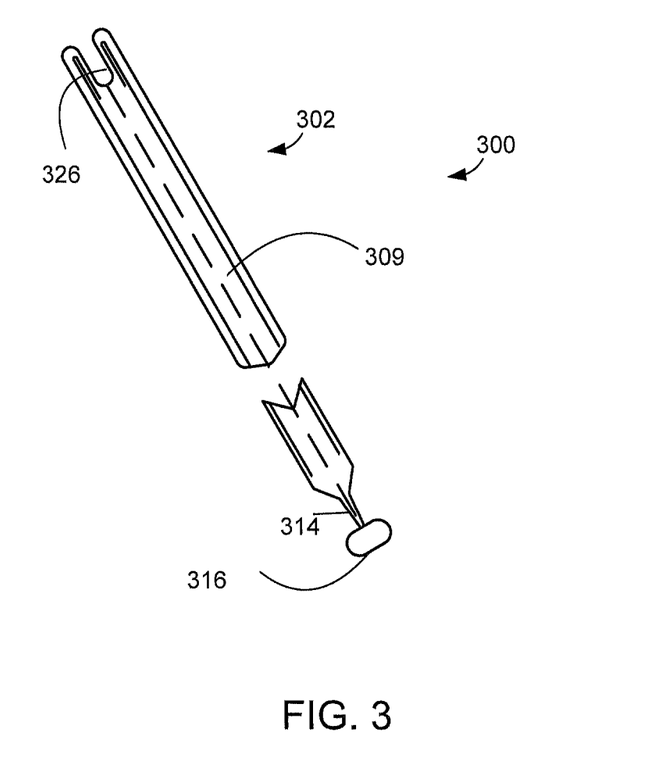
FIG. 3 is a schematic view of a further alternative embodiment, according to the present disclosure.

A further embodiment of medical device 300 is depicted in FIG. 3. This embodiment may include a tubular member 302. For purposes of clarity, conductive elements and their associated components, as well as the elongate introduction sheath, are omitted from FIG. 3.

Actuating element 314, for example, may be attached to an inner surface of distal tip 326. As with previous embodiments, the embodiment depicted in FIG. 3 may include any of the features described in connection with the other embodiments disclosed herein. For example, actuating element 314 may be configured to move distally and proximally in response to movements of handle 316. A proximally directed force may be applied to distal tip 326 such that the distal tip 326 may be pulled into lumen 309, effectively shortening area of the tubular member 302 that is in contact with airway tissue. As handle 316 continues to pull distal tip 326 proximally, the effective energy transfer area of tubular member 302 becomes progressively shorter. In this manner, the amount of energy being transferred to the airway can be controlled, for example. In some embodiments, circuit elements can come in and out of electrical connection, depending on the degree to which distal tip 326 has been pulled into lumen 309.

In another embodiment, for example, actuating element 314 may be configured to evert a distal end of tubular member 302. In such an embodiment, a distal end of tubular member 302 may taper to a relatively smaller diameter (when compared to a remainder of tubular member 302) when fully everted. The smaller diameter may facilitate advancing tubular member 302 into relatively smaller airways, such as, e.g., branch airways. Further, the conductive elements 112 on the portion of tubular member 302 configured to evert may be spaced further apart from one another as compared to the spacing of the electrodes from each other on non-everting portions of tubular member 302.

Piston element 114 may be temporarily or permanently attached to the proximal end 108 of tubular member 102. For temporary attachment, the proximal end 108 may include threading, projections, grooves, a screw-fit, Luer lock, snap-fit, or compression fit arrangement. Permanent attachment may include welding, gluing, soldering, or other forms of attachment. The attachment section may be adjustable, allowing operators to connect tubular members of varying diameters to the piston element 114. For instance, the attachment section may be formed of a flexible or elastic material, such as, e.g., rubber, which may expand radially to allow the piston element 114 to fit into tubular member 102. It will be understood that the attachment section can be made from different materials and be configured differently to provide for adjustability without departing from the scope of the present disclosure.

In some scenarios, the piston element 114 can be constructed as a varistor to protect the entire medical device 100 against excessive voltages or it may regulate voltage for proper functioning of the medical device 100. In other embodiments, the piston element 114 may be configured as other electrical components, including, but not limited to, a rheostat or a variable capacitor. For example, in embodiments relying on AC current, a rheostat or a variable capacitor may function to tune tubular member 102 to deliver energy to selectively deliver energy to specific conductive elements 112. A feedback signal also may be sent by the rheostat or variable capacitor to a controller for the purposes of monitoring treatment. In addition, smaller diameter airways may have different resonance frequencies as compared to larger diameter airways. The rheostat or variable capacitor may be configured to change a treatment frequency so that device 100 may be capable of treating airways of differing sizes.

Alternatives to the embodiments presented in FIGS. 1-3 can be envisioned and implemented by those having skill in the art. For example, the presented embodiments of FIGS. 1 and 2 depend on piston elements 114 and 214 to establish contact with particular sets of conductive bands. In alternative embodiments, energy can be provided to all sets, and the actions of piston elements 114 and 214 can serve to break contact with particular circuits. Other examples of possible combinations will be clear to those of skill in the art.

In addition, various safety measures can be implemented as desired. For example, heat sensors can be provided at various points on tubular members 102, 202, 302 to ensure that temperatures do not rise above preset limits. In another example, circuit breakers may be provided to protect the electric circuit from damage due to overloads, short circuits, and similar problems. In a similar manner, voltage sensors may be provided. In some embodiments, the tubular members 102, 202, may include one or more fenestrations to allow air or blood to flow with minimal obstruction.

Figure 4A:
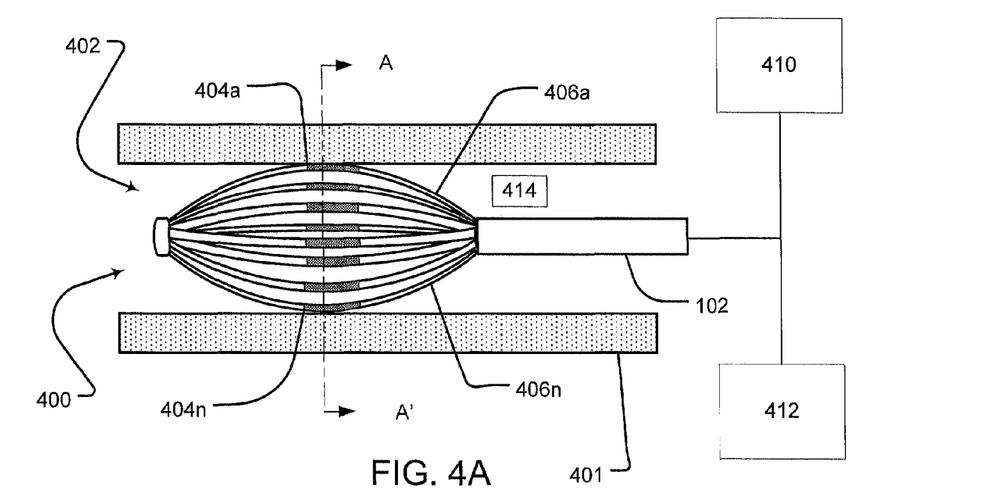
FIG. 4A is a schematic side view of an embodiment showing an expandable basket, according to another embodiment of the present disclosure.

FIG. 4A illustrates a schematic view of a further embodiment of the present disclosure. In the depicted medical device 400, rather than a tubular member, electrical energy may be applied by electrodes 404 carried on a basket assembly 402, having a number of basket legs 406. As may be generally known in the art, basket assembly 402 can assume an expanded form, as illustrated, and a collapsed form, in which basket assembly 402 may be carried within a lumen of introduction sheath. The general structure and operation of basket assembly 402 may be described in, for example, U.S. Pat. No. 7,425,212, entitled "Devices for Modification of Airways by Transfer of Energy", the entirety of which is incorporated herein by reference. General operation and construction of basket assembly 402 will therefore not be discussed further here. It should be noted, however, that the basket may be expandable (that is, expanded by a separate mechanism) or self-expanding (containing an integral mechanism, such as resilient members, or a property, such as being formed of a shape memory alloy). The basket assembly 402 may allow air or blood to flow with minimal obstruction due to its fenestrated structure.

In some embodiments, the basket assembly may be replaced with an expandable member, such as, for example, an inflatable balloon. The balloon may be configured to be inflatable by, e.g., conductive fluid.

The number of basket legs 406 provided with basket assembly 402 may be based on particular therapeutic environments or treatment parameters, so that a particular implementation of the medical device 400 may include basket legs 406*a*-406*n* (collectively, basket legs 406). The illustrated embodiment includes eight legs 406, but other embodiments may include more or fewer legs. Each basket leg 406 may include at least one electrode 404*a*-404*n* (collectively, electrodes 404). Electrodes 404 may be adapted for delivery of various sorts of energy, as described above. Electrodes 404 may be formed integrally with the legs or secured to the legs by a conventional technique, such as soldering, for example. Details of energy sources and connections will not be discussed further here.

Although the amount of expansion of basket assembly 402 may be varied for different-size airway passages 401 it will be apparent that if the same amount of energy is delivered to a smaller airway passage as may be employed for a larger airway passage, the airway passage may be damaged. More particularly, the delivered energy may penetrate deeper into the tissue thickness, thereby potentially destroying, for example, nerve tissue. The medical device 400 provides a mechanism for controlling the amount of energy delivered to airway passages of varying sizes.

For a person skilled in the art it is understood that the principles of this disclosure may be utilized with any suitable lumen within the lumen, including, e.g., blood vessels, biliary lumens, kidney passages, etc.

Medical device 400 may include an energy source 410, a control unit 412, and a sensor element 414. Energy source 410 may be similar to the energy source 106 discussed above, selected to deliver the form of energy required by the planned treatment regime. Control unit 412 may be configured to receive input from components of the medical device 400 as well as from external sources and perform control actions as described below. Sensor element 414 may be a sensor, e.g., a thermocouple, selected to perform the functions described below.

Figure 4B:
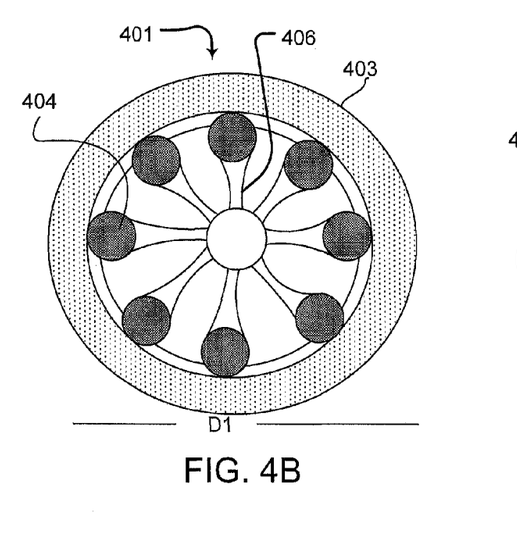
FIGS. 4B and 4C are schematic cross-sectional views illustrating the operation of the system shown in FIG. 4A, taken along plane A-A' of FIG. 4A.
Figure 4C:
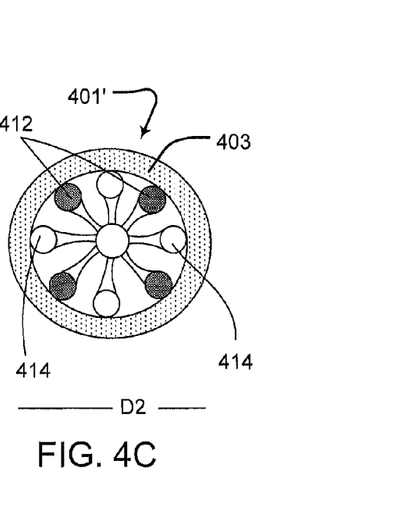

FIGS. 4B and 4C are schematic cross-sectional views taken along the plane A-A' of FIG. 4A, passing through the electrodes 404. There, crosshatching indicates energized electrodes. Thus, FIG. 4B depicts a condition in which all electrodes 404 are energized. In FIG. 4C, however, four electrodes 412 are energized, while the remaining four electrodes 414 are not energized.

Medical device 400 may be configured to vary the energy delivered to an airway 403 by selectively adjusting the number of electrodes that are energized, wherein that number is based on the degree to which the basket assembly 402 expands. As noted above, basket assembly 402 may be carried within the distal end of introduction sheath (not shown) during navigation to a treatment site. After arrival at the treatment site, basket assembly 402 may be advanced beyond the distal end of introduction sheath, at which point it may either self-expand or it may be expanded. In one embodiment, self-expansion may occur because basket legs 406 are formed with a pre-set configuration from a material capable of being compressed to a generally compressed configuration without plastic deformation. Such materials may include, e.g., shape memory alloys, including, but not limited to, nitinol. As all basket legs 406 restore themselves to the expanded configuration, basket assembly 402 may expand until each leg makes contact with wall 403 of airway passage 401. Other modes of expansion, such as expansion by employing a balloon device within basket assembly 402, may be employed as desired and such variations are within the ability of those in the art to design and deploy.

The results of this differential expansion can be seen in comparing FIG. 4B with FIG. 4C. It can be observed that airway passage 401 in the former example has a significantly larger diameter than the airway passage 401' of FIG. 4C. In both situations, however, basket assembly 402 may be configured to expand to the point where legs 406 make contact with wall 403.

To determine how many electrodes to energize, the medical device 400 may include sensor element 414 to sense the degree of basket expansion, for example. In another embodiment, the sensor element 414 may be configured to sense the impedance of the electrodes 404, which will be affected by the spacing of electrodes 404. Further, as those of ordinary skill in the art will recognize, impedance measurement may be accomplished by inducing a sampling current into tissue. For example, in some embodiments, a sampling current may be induced by a first set of electrodes and a second set of electrodes may be configured to sense the sampling current through the tissue. In some cases, the second set of electrodes may be different from the first set of electrodes. In other cases, the second set of electrodes may be the same as the first set of electrodes.

In further examples, a sensor may sense the temperature of airway tissue and/or energy delivered to the tissue. Based on the sensed information, a control unit 412 may select the electrodes 404 to energize. For example, in a narrow airway of about 2 mm, the basket assembly 402 expands a relatively small distance, and spacing between electrodes 404 may be small, which may dictate deactivating every other electrode to reduce applied energy density. The resulting treatment regimen effectively applies energy to the airway while minimizing the danger of damage to tissue outside of the desired treatment depth. As shown, four electrodes 412 may be active and four electrodes 414 may be de-activated. Where the airway may be larger, such as about 8 mm in diameter, as seen in FIG. 4B, the basket assembly 402 expands to a relatively greater extent; accordingly, spacing between each electrode 404 increases, so that sensor element 414 allows all eight electrodes 404 to be active.

A number of techniques may be implemented for determining the degree to which the basket assembly 402 expands, in addition to the technique based on impedance monitoring. For example, expansion causes the individual basket legs 406 to change shape, and therefore a strain gauge (not shown) could be mounted on one or more basket legs 406. The strain gauge may be configured to measure the degree of strain on, for example, a basket leg, which may correspond to basket expansion. Other methods will be apparent to those of ordinary skill in the art.

Figure 4D:
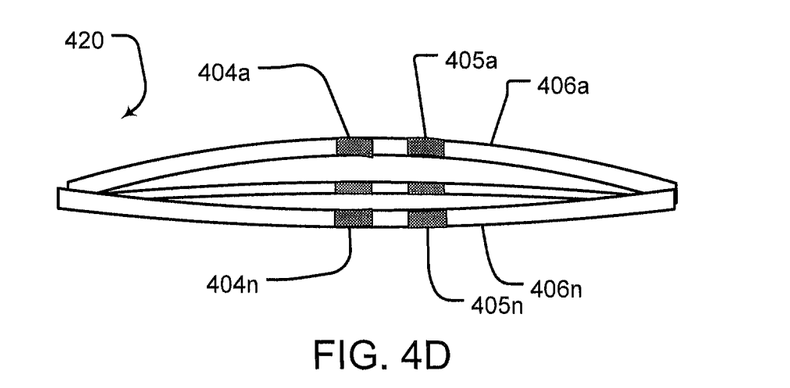
FIGS. 4D and 4E are schematic side views of an embodiment employing the expandable basket shown in FIG. 4A.
Figure 4E:
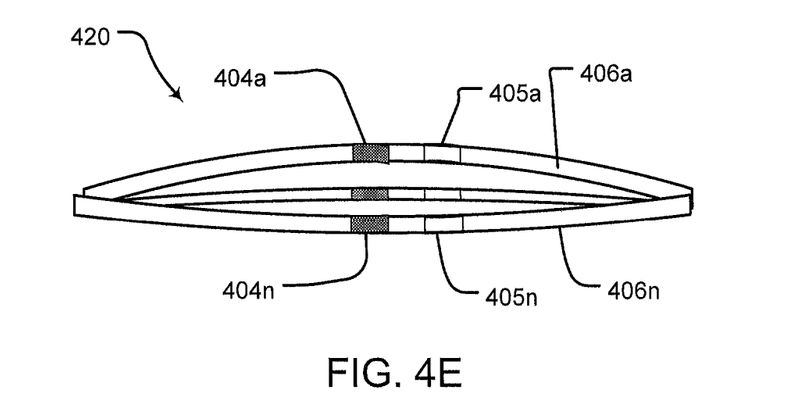

FIGS. 4D and 4E are exemplary side views of a further embodiment 420 of the system shown in FIG. 4A. It will be appreciated that different patient airways may require treatment over different lengths of airway tissue. Embodiment 420 addresses that situation by providing multiple electrodes 404, 405 longitudinally spaced along each leg 406. Taken together, electrodes 404 and 405 define separate sets of electrodes, which can be selectively activated in tandem by control unit 412. Where the physician determines that treatment may be required along a relatively long portion of tissue, such as, for example, 12 mm, as shown in FIG. 4D, electrodes 404a-404n as well as electrodes 405a-405n may be activated (as indicated by crosshatching). That configuration produces energy delivery to tissues along the entire combined length of electrodes 404-405. Although the depicted embodiment shows that electrodes 404 and 405 may be spaced from one another, electrodes 404 and 405 may be disposed directly next to one another, or at any suitable distance from each other. Where the tissue to be treated stretches over a relatively short distance, a single set of electrodes 404a-404n, for example, can be activated, as shown in FIG. 4E. A number of techniques may be available for selecting and applying energy to individual sets of electrodes, as will be clear to those of skill in the art. For example, the physician can provide input to control unit 412 to select a particular group of electrodes.

Figure 4F:
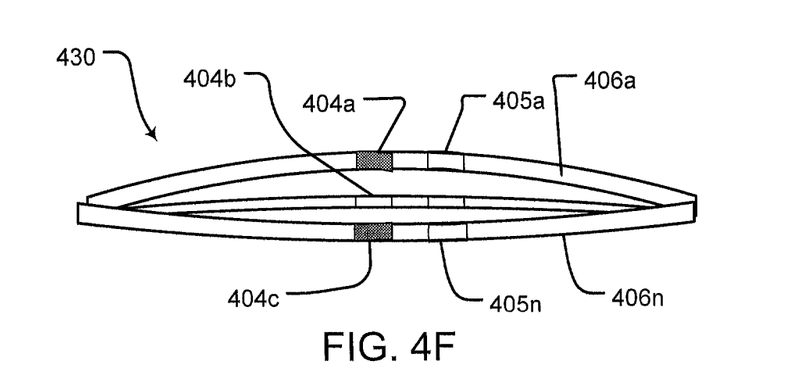
FIG. 4F is a schematic side view of yet another embodiment employing the expandable basket shown in FIG. 4A.

FIG. 4F may be an exemplary view of a further embodiment 430 of the present disclosure, which combines the ability to vary the energy applied based on both the longitudinal distance of the required treatment area as well as the diameter of the airway. This embodiment includes the techniques discussed above in connection with FIGS. 4A-4E. The illustrated embodiment 430 addresses a situation in which treatment may be desired over a relatively short longitudinal stretch of airway (for example, about 4-6 mm) and, additionally, the system's sensing element has detected a relatively small expansion of the basket assembly 402. Based on the first factor, electrodes 404 are selected for activation while electrodes 405 are turned off. Based on the airway diameter, as indicated by the degree of basket assembly 402 expansion, electrodes 404a and 404c are activated, while electrode 404b may be turned off. As with previous illustrations, electrode activation is indicated by crosshatching.

It will be appreciated that a number of control elements may be required by the embodiments shown in connection with FIGS. 4A-4F. Design and implementation of such elements may be well within the skill of those in the art, and those details do not require discussion here.

Those skilled in the art will recognize that the present disclosure may be implemented in a variety of forms other than the specific embodiments described and contemplated herein. Accordingly, departure in forms and detail may be made without departing from the scope and spirit of the present disclosure as described in the appended claims.

What is claimed is:

1. A medical device for treating tissue, the device comprising:
    an expandable member movable between a collapsed configuration and one or more expanded configurations, the expandable member including a plurality of energy delivery elements, wherein at least some of the energy delivery elements are configured to be activated separately from a remainder of the energy delivery elements; and
    a control unit configured to receive an impedance measurement from a sensor unit or from at least one of the plurality of energy delivery elements, wherein the control unit is configured to determine a degree of expansion of the expandable member based on the impedance measurement, and wherein the control unit is configured to selectively activate the plurality of energy delivery elements based on the determined degree of expansion.

2. The medical device of claim 1, wherein the control unit is configured to activate a first number of the plurality of energy delivery elements when the control unit determines, based on the impedance measurement, that the expandable member is at a first expanded configuration, and activate a second number of the plurality of energy delivery elements when the control unit determines, based on the impedance measurement, that the expandable member is at a second expanded configuration.

3. The medical device of claim 2, wherein the second number is greater than the first number, and a diameter of the expandable member is greater while in the second expanded configuration than while in the first expanded configuration.

4. The medical device of claim 2, wherein the control unit is configured to activate all of the plurality of energy delivery elements when the control unit determines, based on the impedance measurement, that the expandable member is in the second expanded configuration.

5. The medical device of claim 2, wherein the control unit is configured to active only alternating energy delivery elements of the plurality of energy delivery elements when the control unit determines, based on the impedance measurement, that the expandable member is in the first expanded configuration.

6. The medical device of claim 1, wherein at least two of the plurality of energy delivery elements are radially spaced apart from one another.

7. The medical device of claim 1, wherein at least two of the plurality of energy delivery elements are longitudinally spaced apart from one another.

8. The medical device of claim 1, wherein the energy delivery elements are electrodes configured to deliver RF energy.

9. The medical device of claim 1, wherein the expandable member is an expandable basket.

10. The medical device of claim 9, wherein the expandable basket includes a plurality of legs, wherein each of the plurality of legs includes one or more of the plurality of energy delivery elements.

11. The medical device of claim 10, wherein distal ends of the plurality of legs converge toward one another.

12. The medical device of claim 1, further including an elongate tubular member having a proximal end, a distal end, and a lumen extending therebetween, wherein the expandable member is disposed in the lumen when in the collapsed configuration, and the expandable member is configured to expand as it is deployed from the distal end of the elongate tubular member.

13. A medical device for treating tissue, the device comprising:
   an expandable member movable between a collapsed configuration and one or more expanded configurations, the expandable member including a plurality of energy delivery elements; and
   a control unit configured to receive an impedance measurement from a sensor unit or from at least one of the plurality of energy delivery elements, and wherein the control unit is configured to activate only some of the plurality of energy delivery elements when the control unit determines, based on the impedance measurement, that the expandable member is expanded to a first diameter, and wherein the control unit is configured to activate all of the plurality of energy delivery elements when the control unit determines, based on the impedance measurement, that the expandable member is expanded to a second diameter, wherein the second diameter is greater than the first diameter.

14. The medical device of claim 13, wherein the control unit is configured to active only alternating energy delivery elements of the plurality of energy delivery elements when the control unit determines that the expandable member is expanded to the first diameter.

15. The medical device of claim 13, wherein at least two of the plurality of energy delivery elements are radially spaced apart from one another.

16. The medical device of claim 13, wherein at least two of the plurality of energy delivery elements are longitudinally spaced apart from one another.

17. The medical device of claim 13, wherein the energy delivery elements are electrodes configured to deliver RF energy.

18. A medical device for treating tissue, the device comprising:
   an expandable member movable between a collapsed configuration and one or more expanded configurations, the expandable member including a plurality of energy delivery elements that are configured to deliver RF energy, wherein at least some of the energy delivery elements are configured to be activated separately from a remainder of the energy delivery elements, and wherein the expandable member is an expandable basket including a plurality of legs, wherein each of the plurality of legs includes one or more of the plurality of energy delivery elements; and
   a control unit configured to receive an impedance measurement from a sensor unit or from at least one of the plurality of energy delivery elements, wherein the control unit is configured to determine a degree of expansion of the expandable member based on the impedance measurement, and wherein the control unit is configured to selectively activate the plurality of energy delivery elements based on the determined degree of expansion,
   wherein the control unit is configured to activate only some of the plurality of energy delivery elements when the control unit determines, based on the impedance measurement, that the expandable member is at a first expanded configuration, and activate all of the plurality of energy delivery elements when the control unit determines, based on the impedance measurement, that the expandable member is at a second expanded configuration, and
   wherein a diameter of the expandable member is greater while in the second expanded configuration than while in the first expanded configuration.

19. The medical device of claim 18, wherein the control unit is configured to active only alternating energy delivery elements of the plurality of energy delivery elements when the control unit determines that the expandable member is in the first expanded configuration.

* * * * *